United States Patent [19]
Yuuchi et al.

[11] Patent Number: 5,146,920
[45] Date of Patent: Sep. 15, 1992

[54] WIRELESS LOW-FREQUENCY MEDICAL TREATMENT DEVICE WITH PULSE INTERRUPTION BASED UPON ELECTRODE CONTACT WITH THE BODY

[75] Inventors: Takahiro Yuuchi; Yasuyuki Tsuchida, both of Hyogo; Masakatsu Fujiwara, Kasai, all of Japan

[73] Assignee: Sanyo Electric Co., Ltd, Osaka, Japan

[21] Appl. No.: 614,172

[22] Filed: Nov. 15, 1990

[30] Foreign Application Priority Data

Nov. 20, 1989 [JP] Japan .................. 1-302944

[51] Int. Cl.$^5$ .......................... A61N 1/36; A61N 1/08
[52] U.S. Cl. .................. 128/423 R; 128/421; 128/908
[58] Field of Search ............ 128/423 R, 421, 422, 128/734, 908, 903, 423

[56] References Cited

U.S. PATENT DOCUMENTS

| | | | |
|---|---|---|---|
| 3,241,557 | 3/1966 | Masaki | 128/422 |
| 3,489,152 | 1/1970 | Barbara | 128/422 |
| 3,645,267 | 2/1972 | Hagfors | 128/421 |
| 3,796,221 | 3/1974 | Hagfors | 128/421 |
| 3,886,932 | 6/1975 | Suessmilch | 128/908 |
| 4,088,141 | 5/1978 | Niemi | 128/908 |
| 4,102,348 | 7/1978 | Hihara et al. | 128/422 |
| 4,177,819 | 12/1979 | Kofsky et al. | 128/423 R |
| 4,372,319 | 2/1983 | Ichinomiya et al. | 128/421 |
| 4,459,989 | 7/1984 | Borkan | 128/421 |
| 4,524,774 | 6/1985 | Hildebrandt | 128/421 |

Primary Examiner—William E. Kamm
Assistant Examiner—Kennedy J. Schaetzle
Attorney, Agent, or Firm—Armstrong & Kubovcik

[57] ABSTRACT

A wireless low-frequency medical treatment device having a sending section for sending various data for low-frequency medical treatment and a pulse applying section for receiving the above data, for generating a low-frequency pulse corresponding to the data and for applying the pulse on a living body, the device being characterized in that the pulse applying section comprises a plurality of pulse applying bodies to be pasted on the living body; a low-frequency pulse generating device for generating a low-frequency pulse to be supplied to the pulse applying bodies in accordance with data sent from the sending section; a detecting device for detecting that at least one of the pulse applying bodies comes off from the living body; a pulse stopping device for stopping generation of the low-frequency pulse when the detecting device detects that at least one of the pulse applying bodies comes off from the living body; and a pulse recovery device for increasing a potential of the low-frequency pulse gradually from a low level to a predetermined high level when both of the pulse applying bodies are pasted on the living body after at least one of the pulse applying bodies comes off once.

26 Claims, 5 Drawing Sheets

WIRELESS LOW-FREQUENCY MEDICAL TREATMENT DEVICE WITH PULSE INTERRUPTION BASED UPON ELECTRODE CONTACT WITH THE BODY

BACKGROUND OF THE INVENTION (1) Field of the Invention

This invention relates to a wireless low-frequency medical treatment device for applying desirable treatment by conveying data for the treatment to a pulse applying section which is pasted on the living body (2) Description of the Prior Art Japanese Patent Publication Laid-Open No. 63-317164 discloses a known low-frequency medical treatment device of this kind, in which data for desirable treatment is conveyed from an input section to a pulse applying section pasted on the living body by FM waves.

In this type of device, the input section and the pulse applying section are not connected to each other by a lead or the like. Therefore, it is not detected by the device if the pulse applying section comes off from the human body during operation. If the pulse applying section is pasted again in such case without stopping the operation of the input section, which is still in the state of outputting a strong electric stimulating pulse, the human body is exposed to danger.

SUMMARY OF THE INVENTION

Accordingly, this invention has an object of offering a wireless low-frequency medical treatment device which gives no strong electric shock to the living body even if a pulse applying section is pasted on the living body after coming off once.

The above object is fulfilled by a wireless low-frequency medical treatment device having a sending section for sending various data for low-frequency medical treatment and a pulse applying section for receiving the above data, for generating a low-frequency pulse corresponding to the data and for applying the pulse on a living body, the device being characterized in that the pulse applying section comprises a plurality of pulse applying bodies to be pasted on the living body; a low-frequency pulse generating device for generating a low-frequency pulse to be supplied to the pulse applying bodies in accordance with data sent from the sending section; a detecting device for detecting that at least one of the pulse applying bodies comes off from the living body; a pulse stopping device for stopping generation of the low-frequency pulse when the detecting device detects that at least one of the pulse applying bodies comes off from the living body; and a pulse recovery device for increasing a potential of the low-frequency pulse gradually from a low level to a predetermined high level when both f the pulse applying bodies are pasted on the living body after at least one of the pulse applying bodies comes off once.

The plurality of pulse applying bodies may be a first applying body and a second applying body; and the detecting device may detect that at least one of the pulse applying bodies comes off from the living body based on whether a detecting current flows through a detecting current path including the living body and the first and the second pulse applying bodies.

The low-frequency pulse generating device may comprise a voltage pulse generating device for generating voltage pulses periodically for a length of time determined by the data sent from the sending section; an accumulating device for accumulating the voltage pulses; and a switching device for alternately turning on and off a pulse supplying path which extends from the accumulating device to the first pulse applying body in order to supply the accumulated voltage pulses.

The voltage pulse generating device may comprise a voltage enhancing inductor and a voltage inducing device for electrifying the voltage enhancing inductor periodically to induce enhanced voltages; and the accumulating device may comprise a capacitor.

The switching device may comprise a first switching element for applying the voltage pulses accumulated by the accumulating device to the first pulse applying body periodically; and a second switching element for being conductive and keeping the second pulse applying body grounded while the first switching element is applying the voltage pulses.

The detecting current path may comprise a series circuit including a resistance for converting the detecting current into a voltage, the first pulse applying body, the living body, the second pulse applying body and the second switching element in this order.

The pulse stopping device may comprise a control circuit for stopping the operation of the voltage pulse generating device and for keeping the switching device off.

The pulse recovery device may comprise a judging device for judging that both of the pulse applying bodies are pasted back on the living body after at least one of the bodies comes off once; and a time length changing device for, when the judging device judges both of the pulse applying bodies are pasted back, turning on and off alternately the voltage pulse generating device for a time length which is microscopic and for gradually extending the time length until the time length reaches a predetermined level.

The low-frequency pulse generating device may comprise a voltage pulse generating device for generating voltage pulses periodically for a length of time determined by the data sent from the sending section, an accumulating device for accumulating the voltage pulses, a pair of switching devices for alternately turning on and off a pulse supplying path which extends from the accumulating device to the first pulse applying body in order to supply the accumulated voltage pulses; and a control device for selectively turning active one of the pair of the switching devices.

The first and the second switching devices may each have a first switching element which is turned on and off alternately when the device is turned active by the control device and a second switching element which is kept conductive while the device is active; the first switching element of the first switching device may supply the voltage pulses accumulated by the accumulating device to the first pulse applying body when being turned on, and the first switching element of the second switching device may supply the voltage pulses accumulated by the accumulating device to the second pulse applying body when being turned on; and the second switching element of the first switching device may ground the second pulse applying body when being conductive, and the second switching element of the second switching device may ground the first pulse applying body when being conductive.

The detecting current path may comprise a series circuit which includes a first resistance for converting a detecting current into a voltage, the first pulse applying body, the living body, the second pulse applying body, and the second switching element of the first switching device in this order when the first switching device is active; and may comprise a series circuit which includes a second resistance for converting a detecting current into a voltage, the second pulse applying body, the living body, the first pulse applying body, and the second switching element of the second switching device in this order when the second switching device is active.

The pulse stopping device may comprise a control circuit for stopping the operation of the voltage pulse generating device and for keeping the first and the second switching device off.

According to the above construction, the detection device detects if at least one of the pulse applying bodies is off the living body, and if so, the generation of the low-frequency pulses is stopped. After the pulse applying body is pasted back on the living body, the potential of the low-frequency pulses applied on the living body is gradually increased from a very low level up to the level before the body comes off. In this way, the living body is exposed to no shock and the treatment is done safely. Also, since the pulse generating device is stopped while the pulse applying body is off the living body, energy can be saved.

BRIEF DESCRIPTION OF THE DRAWINGS

These and other objects, advantages and features of the invention will become apparent form the following description thereof taken in conjunction with the accompanying drawings which illustrate a specific embodiment of the invention. In the drawings.

DESCRIPTION OF A PREFERRED EMBODIMENT

A construction of an embodiment according to this invention will be described referring to FIGS. 1 through 3. A wireless low-frequency medical treatment device comprises a sending section 100 and a pulse applying section 200. The sending section 100 comprises a key input part 1 and a signal output part 2 (FIG. 3).

Figure 1:
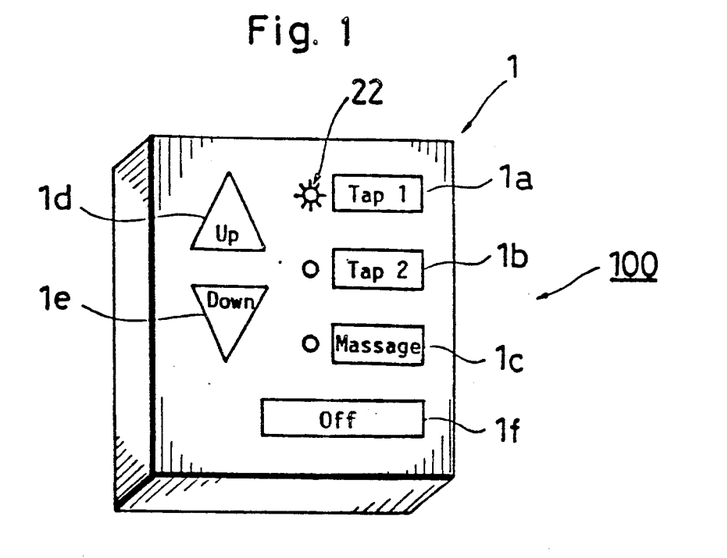
FIG. 1 is an outer view of a sending section of an embodiment according to this invention.

As shown in FIG. 1, the key input part 1 has keys $1a$, $1b$ and $1c$ respectively for "Tap 1", "Tap 2" and "Massage" modes, keys $1d$ and $1e$ respectively for "Up" and "Down", and a key $1f$ for "Off".

The signal output part 2 comprises a microcomputer 20 for processing data sent from the key input part 1, a converter 21 for converting a signal sent from the microcomputer 20 into a magnetic field, and a display 22 including LEDs for indicating which mode has been selected or the like.

Figure 3:
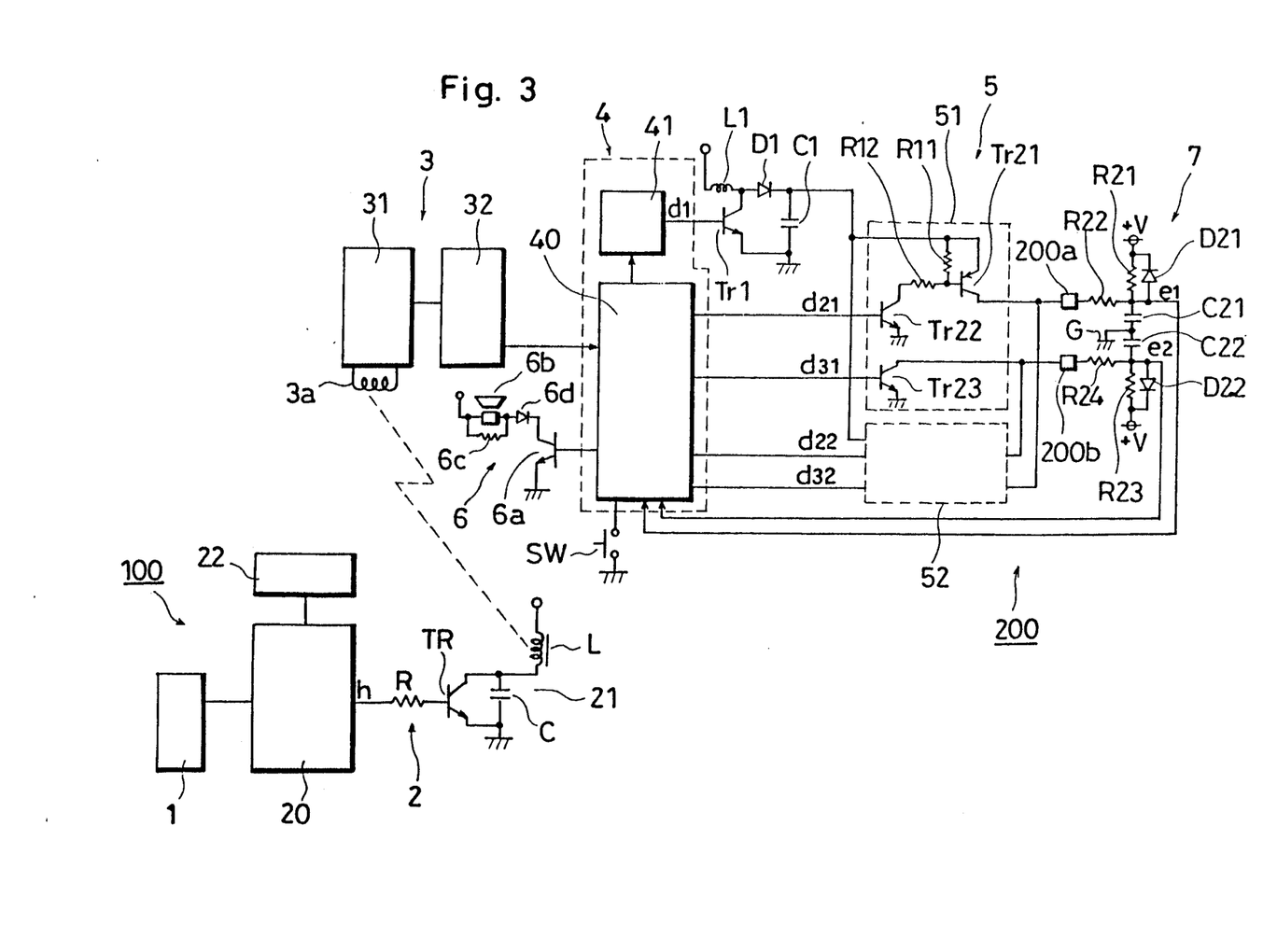
FIG. 3 is a circuit diagram of the embodiment.

As shown in FIG. 3, the converter 21 comprises a resistance R, a transistor Tr, a capacitor C and an induction coil L as a sending coil.

Figure 2A:
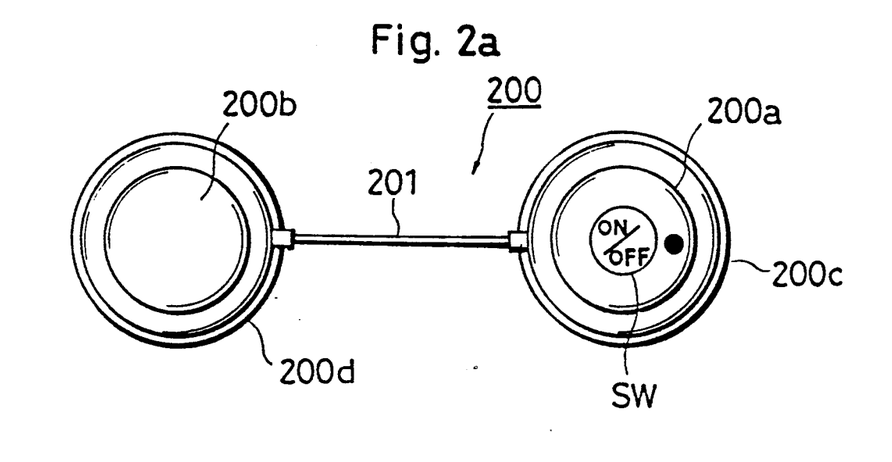
FIG. 2a is a plan view of a pulse applying section of this embodiment.
Figure 2B:
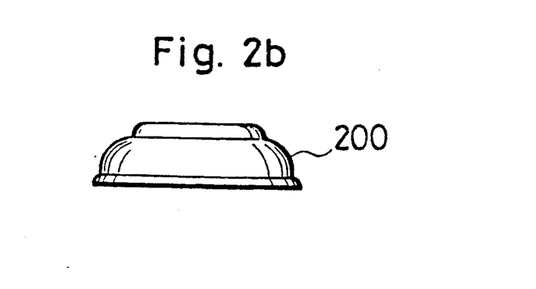
FIG. 2b is a side view thereof.

As shown in FIGS. 2a and 2b, the pulse applying section 200 comprises a pair of pulse applying bodies 200a and 200b and a lead 201 for connecting the bodies.

In FIG. 3, 3 refers to a relaying circuit, 4 to a signal processor, 5 to a pulse generating circuit, 6 to a beep sounding circuit, and 7 to a skin detector The relaying circuit 3 comprises a magnetic/electric converter (will be referred to as the converter) 31 and a low-pass filter 32. The converter 31 is for converting a signal which is sent from the sending section 100 to an induction coil $3a$ as a receiving coil by electromagnetic induction into an electric signal; and the low-pass filter 32 is for taking out data from the electric signal sent from the converter 31.

The signal processor 4 comprises a microcomputer 40 and an oscillator 41. The microcomputer 40 is for sending a signal to the oscillator 41, sending driving pulses $d_{21}$, $d_{31}$, $d_{22}$ and $d_{32}$ to the pulse generating circuit 5 and controlling the beep sounding circuit 6; and the oscillator 41 is for outputting a specified driving pulse $d_1$ in accordance with the signal sent from the microcomputer 40.

The pulse generating circuit 5 is for outputting a low-frequency pulse as an electric stimulating pulse in accordance with the driving pulses $d_1$, $d_{21}$, $d_{31}$, $d_{22}$, and $d_{32}$. The circuit 5 comprises a transistor Tr1 to be switched by the driving pulse $d_1$, an induction coil L1 connected between a power source and a collector of the transistor Tr1, a capacitor C1 connected through a diode D1 between an emitter and the collector of the transistor Tr1, a first switching circuit 51 and a second switching circuit 52. The first switching circuit 51 comprises three transistors Tr21, Tr22 and Tr23 and two resistances R11 and R12. The second switching circuit 52 has the same construction though not shown in FIG. 3. These two switching circuits are provided in order to switch the polarity of the low-frequency pulse which is outputted to the pulse applying bodies 200a and 200b.

The beep sounding circuit 6 comprises a transistor $6a$ to be switched by the signal from the microcomputer 40, a beeper $6b$, a resistance $6c$ connected to the beeper $6b$ in parallel, and a diode $6d$ connected between the transistor $6a$ and the beeper $6b$.

The skin detector 7 comprises a resistance R21, a diode D21 connected to the resistance R21 in parallel, a resistance R22 connected between the pulse applying body 200a and an anode of the diode D21, a capacitor C21 connected between the anode of the diode D21 and a ground G, a resistance R23, a diode D22 connected to the resistance R23 in parallel, a resistance R24 connected between the pulse applying body 200b and an anode of the diode D22, and a capacitor C22 connected between the anode of the diode D22 and the ground G.

The relaying section 3 including the induction coil $3a$ is integrated in the pulse applying body 200b; and the signal processor 4, the pulse generating circuit 5, the beep sounding circuit 6, the skin detector 7, and a cell as the power source are integrated in the pulse applying body 200a.

The wireless low-frequency medical treatment device having the above construction is operated as indicated in FIGS. 4 through 9.

Figure 4:
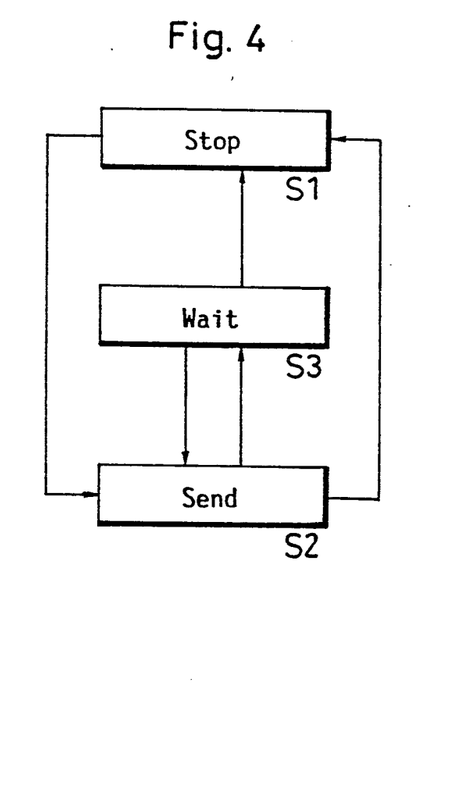
FIG. 4 is a state transition diagram of the sending section.

FIG. 4 is a state transition diagram of the sending section 100. The microcomputer 20 is stopped in the initial state (S1). When the key 1a, 1b or 1c is pushed, a clock oscillation puts the microcomputer 20 into a sending state (S2), whereby a built-in timer is started. Simultaneously, an LED is lighted up in the display 22 in accordance with the key pushed. If the key 1d or 1e is pushed in the initial state, the microcomputer 20 is kept stopped.

When the key 1a for "Tap 1" is pushed, for example, the following operation is executed.

Figure 5:
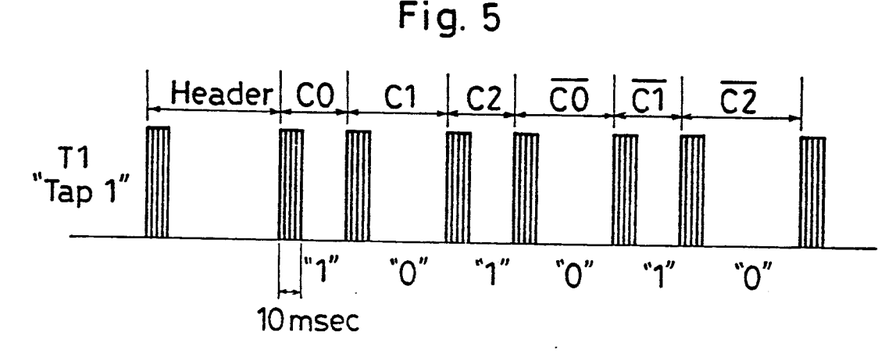
FIG. 5 shows a waveform of a signal sent from the sending section.

First, the microcomputer 20 sends a corresponding code h to the converter 21, thereby supplying a resonating current i to the induction coil L and the capacitor C. Then, the induction coil L outputs a sending signal T1 for "Tap 1" to the converter 31 by a 5 kHz carrier wave. As shown in FIG. 5, the sending signal T1 comprises a header pulse and a pulse code line, wherein [C0 C1 C2 $\overline{C0}$ $\overline{C1}$ $\overline{C2}$] is [101010]. Each pulse is approx. 10 msec wide, and the induction coil L resonates through each pulse. The sending signals T2 through T6 for the other keys have the following pulse code lines.

TABLE 1

|  | C0 | C1 | C2 | C0 | C1 | C2 |
|---|---|---|---|---|---|---|
| Tap 1 (T1) | 1 | 0 | 1 | 0 | 1 | 0 |
| Tap 2 (T2) | 1 | 0 | 0 | 0 | 1 | 1 |
| Massage (T3) | 1 | 1 | 0 | 0 | 0 | 1 |
| Up (T4) | 0 | 1 | 1 | 1 | 0 | 0 |
| Down (T5) | 0 | 0 | 1 | 1 | 1 | 0 |
| Off (T6) | 0 | 1 | 0 | 1 | 0 | 1 |

When the sending signal is sent out to the converter 31, the microcomputer 20 gets into a waiting state for key input (S3). In this state, any of the keys 1a through 1f can be pushed. Every time the key 1a, 1b or 1c is pushed, the timer of the microcomputer 20 is cleared. When the timer detects a specified period of time has passed, the microcomputer 20 sends a code for "Off" to the converter 21 and stops operating.

Figure 6:
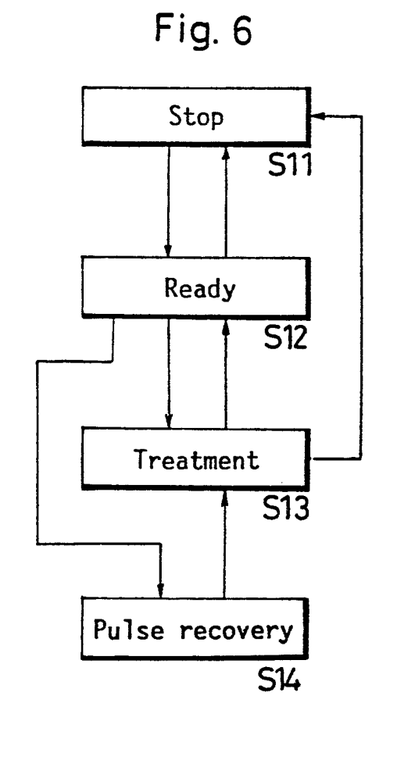
FIG. 6 is a state transition diagram of the pulse applying section.
Figure 7:
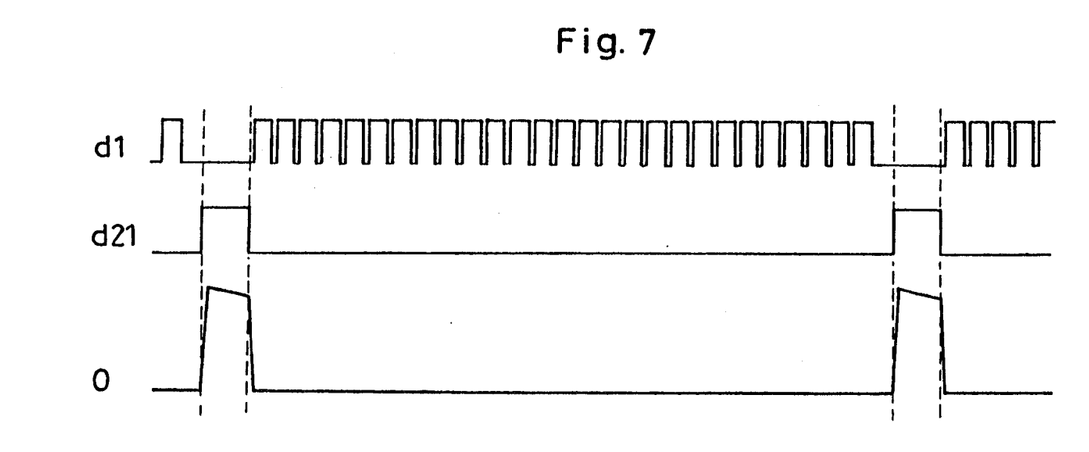
FIG. 7 shows waveforms of driving pulses $d_1$ and $d_{21}$ and a low-frequency pulse when the number of the driving pulse $d_1$ is large.

FIG. 6 is a state transition diagram of the pulse applying section 200. The microcomputer 40 is stopped in the initial state (S11), wherein no command is accepted. When an ON/OFF switch provided on an upper surface of the body 200a is pushed, a built-in clock is oscillated, thereby the microcomputer 40 goes into a ready state (S12), wherein only reception of commands is possible In the ready state, in other words, a data which is taken out by the low-pass filter 32 from the sending signals sent from the converter 31 is not accepted by the microcomputer 40, but the microcomputer 40 is waiting for an operation command or waiting for detection signals e1 and e2 outputted by the skin detector 7 to get low. If the ready state is kept for a specified period (for example, 3 minutes), the microcomputer 40 stops operating in order to prevent the wasted use of the cell.

When the key 1a, 1b or 1c is pushed with the detection signals e1 and e2 being low or when the detection signals e1 and e2 get low with the above key being pushed in the ready state, the microcomputer 40 goes into a treatment state (S13).

It is when both of the pulse applying bodies 200a and 200b are pasted on the human body that the detection signals e1 and e2 get low.

In more detail, when the first switching circuit 51 is active, the driving pulse $d_{31}$ is high and the transistor Tr23 is conductive. Therefore, the pulse applying body 200b is kept at the ground potential through the transistor Tr23 between a collector and an emitter thereof. If the pulse applying bodies 200a and 200b are both pasted on the human body, a current flows from the power source to the resistance R21, the resistance R22, the pulse applying body 200a, the human body, the pulse applying body 200b and the transistor Tr23 in this order. Accordingly, the potentials of the detection signals e1 and e2 are lower than the power source +V by the amount which has been reduced by the resistance R21 and R23, respectively. On the other hand, if at least one of the pulse applying bodies 200a and 200b is off from the human body, no current flows in the above way. Accordingly, the potential of the detection signal e1 is as high as the power source +V.

When the second switching circuit 52 is active, the driving pulse $d_{32}$ is high and a built-in transistor is conductive. Therefore, the pulse applying body 200a is kept at the ground potential. If the pulse applying bodies 200a and 200b are both pasted on the human body, the potentials of the detection signals e1 and e2 are low. On the other hand, if at least one of the pulse applying bodies 200a and 200b is off from the human body, the potential of the detection signal e2 is as high as the power source +V.

The first switching circuit 51 and the second switching circuit 52 are alternately turned active periodically by the microcomputer 40.

The microcomputer 40 detects the state of the detection signals e1 and e2, namely, whether the pulse applying bodies 200a and 200b are pasted on the human body or not.

In the treatment state, the oscillator 41 is operated in accordance with a data sent from the low-pass filter 32, and driving pulses $d_{21}$ and $d_{22}$ are sent to the pulse generating circuit 5. Simultaneously, the microcomputer 40 sends a signal to the beep sounding circuit 6, thereby to emit one (for example) beep from the beeper 6b. The oscillator 41 sends a driving pulse $d_1$ (FIG. 7) to the first transistor Tr1 in accordance with a signal from the microcomputer 40. The transistor Tr1 is turned on or off by the driving pulse $d_1$, thereby to allow an exciting current to be sent from the power source to the induction coil L1 periodically. Voltages enhanced by the exciting current are accumulated in the capacitor C1 through the diode D1. When the driving pulse $d_{21}$, for example, gets high, the transistors Tr21 and Tr22 are turned on. Accordingly, the voltages accumulated in the capacitor C1 are applied on the human body as low-frequency stimulating pulses 0, the human body being between the bodies 200a and 200b. Incidentally, the driving pulses $d_{21}$ and $d_{22}$ each are on, for example, for 20 μsec. and off, for example, for 720 msec.

Figure 8:
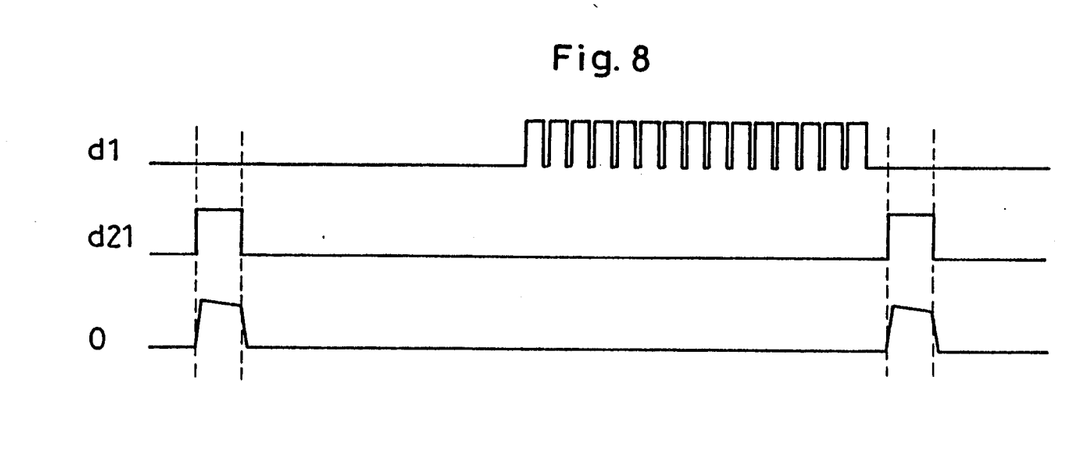
FIG. 8 shows waveforms of driving pulses $d_1$ and $d_{21}$ and a low-frequency pulse when the number of the driving pulse $d_1$ is small.

The driving pulse $d_1$ is outputted to the first transistor Tr1 when the driving pulse $d_{21}$ is not outputted. As the number of the driving pulse $d_1$ is reduced, the voltages accumulated in the capacitor C1 are reduced, thereby the stimulating pulses O applied on the human body are weakened as shown in FIG. 8.

The strength of the stimulating pulses 0 is determined by the operation of the key 1d or 1e. In more detail, if the key 1d is pushed, for example, the microcomputer 40 commands the oscillator 41 to strengthen the driving pulse $d_1$ and also commands the beep sounding circuit 6 to emit beeps in a way predetermined for "Up" from the beeper 6b.

If a stop is commanded during the treatment, the microcomputer 40 goes into the ready state. If the ready state is kept for a specified period of time (for example, 3 minutes), the microcomputer 40 stops operating. If the ON/OFF switch is pushed during treatment, the microcomputer 40 stops operating and the output of the driving pulses $d_{21}$ and $d_{22}$ is stopped.

If both or either of the bodies 200a and 200b is peeled off from the human body during treatment, the detection signal e1 or e2 gets high, thereby the microcomputer 40 stops operating and goes into the ready state. If the peeled-off body is pasted back on the human body in this state, the detection signal which has been high gets low. Then, a pulse recovery operation is carried out (S14).

Figure 9:
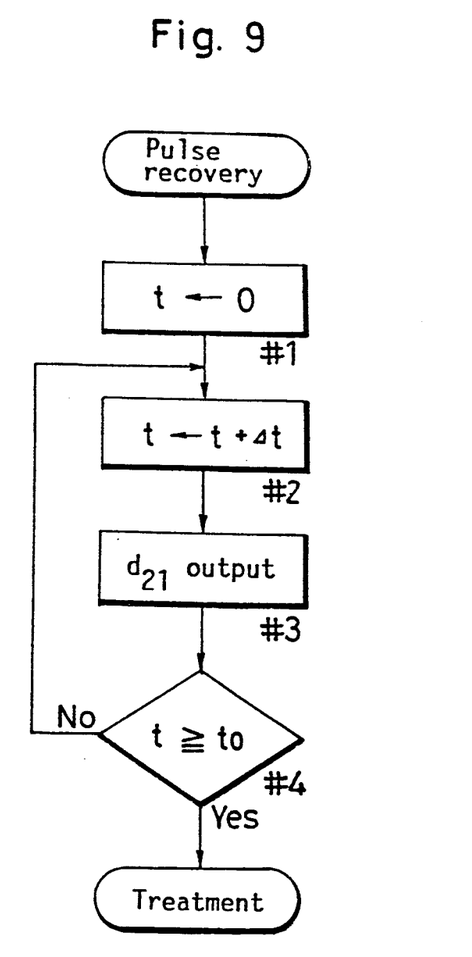
FIG. 9 is a flowchart of the operation which is carried out when the pulse applying section is pasted on the living body after coming off once.

FIG. 9 is a flowchart of the pulse recovery operation. First, the microcomputer 40 is initiated, whereby a time t (namely, the length of time during which the driving pulses $d_1$ are periodically outputted) is 0 (#1). Then, the time t is increased by a microscopic time $\Delta t$ (#2), and the driving pulse $d_{21}$ or $d_{22}$ of the switching circuit 51 or 52, whichever is active, is outputted (#3). The stimulating pulse O is weak at this stage. The time t is further increased by $\Delta t$, and the driving pulse $d_{21}$ (for example) is again outputted. At this time, the stimulating pulse O is a little stronger than the previous one since more voltages are accumulated in the capacitor C1 than the previous time. Such increase of the time t is repeated until the time t reaches a predetermined length $t_o$. Throughout the above repetition, the driving pulses $d_{21}$ are outputted one after another. Each time the time t is increased by $\Delta t$, the accumulated voltages are increased. Accordingly, the stimulating pulses O are applied more and more strongly. When $t=t_o$ (#4), the driving pulses $d_{21}$ are outputted in the same manner as they are before the pulse applying bodies 200a and 200b come off. Accordingly, the stimulating pulses 0 are as strong as those before the coming-off.

The microcomputer 40 carries out the treatment for a specified period of time (for example, 15 minutes) after receiving the data for "Tap 1", "Tap 2" or "Massage" and then goes into the ready state.

The skin detector 7 outputs two detection signals to comply with the two polarities of the low-frequency pulse in the above embodiment. If the polarity of the low-frequency pulse is not to be changed, one detection signal is enough. In this case, only one switching circuit is required.

Instead of one induction coil of the sending section and one induction coil of the relay circuit, two induction coils may be provided in the sending section and two induction coils in the relay circuit. In such case, it is desirable that carrier waves from the induction coils in the sending section are outputted with a 90° phase difference. In this construction, magnetic waves can be outputted in all directions from the sending section and therefore are received by the relaying circuit more easily.

Although the present invention has been fully described by way of an embodiment with references to the accompanying drawings, it is to be noted that various changes and modifications will be apparent to those skilled in the art. Therefore, unless otherwise such changes and modifications depart from the scope of the present invention, they should be construed as being included therein.

What is claimed is:

1. A wireless low-frequency medical treatment device having a sending section for sending various data for low-frequency medical treatment and a pulse applying section for receiving the above data, for generating a low-frequency pulse corresponding to the data and for applying the pulse on a living body, the device being characterized in that the pulse applying section comprises:
   a plurality of pulse applying bodies to be pasted on the living body;
   low-frequency pulse generating means for generating a low-frequency pulse to be supplied to the pulse applying bodies in accordance with data sent from the sending section;
   detecting means for detecting if at least one of the pulse applying bodies comes off from the living body;
   pulse stopping means for stopping generation of the low-frequency pulse when the detecting means detects that at least one of the pulse applying bodies comes off from the living body;
   timer means for measuring a past time after the detecting means detects at least one of the pulse applying bodies having come off from the living body;
   pulse recovery means for increasing a potential of the low-frequency pulse gradually from a low level to a predetermined high level when the pulse applying body once having come off from the living body is pasted again on the living body before a preset time of said timer means has passed;
   state transition controlling means for transiting to a state to stop generation of the pulse after the preset time of said timer means has passed and to refuse the data sent from the sending section.

2. A device according to claim 1, wherein said plurality of pulse applying bodies comprises a first applying body and a second applying body, and said detecting means comprises means for supplying a detecting circuit to said first and second applying bodies, wherein said detecting means detects whether at least one of the pulse applying bodies has come off from the living body based on whether said detecting circuit flows through a detecting current path including the living body and the first and second pulse applying bodies.

3. A wireless low-frequency medical treatment device having a sending section for sending various data for low-frequency medical treatment and a pulse applying section for receiving the above data, for generating a low-frequency pulse corresponding to the data and for applying the pulse on a living body, the device being characterized in that the pulse applying section comprises:
   a plurality of pulse applying bodies to be pasted on the living body, wherein said plurality of pulse applying bodies comprises a first applying body and a second applying body;
   low-frequency pulse generating means for generating a low-frequency pulse to be supplied to the pulse applying bodies in accordance with data sent from the sending section, wherein the low-frequency pulse generating means comprises voltage pulse generating means for generating voltage pulses periodically for a length of time determined by the data sent from the sending section, accumulation means for accumulating the voltage pulses, and switching means for alternately turning on and off a pulse supplying path which extends from the accumulating means to the first pulse applying body in order to supply the accumulated voltage pulses;

detecting means for detecting if at least one of the pulse applying bodies comes off from the living body, wherein said detecting means comprises means for supplying a detecting current to said first and second applying bodies, wherein said detecting means detects whether at least one of the pulse applying bodies has come off from the living body based on whether said detecting current flows through a detecting current path including the living body and the first and second pulse applying bodies;

pulse stopping means for stopping generation of the low-frequency pulse when the detecting means detects that at least one of the pulse applying bodies comes off from the living body; and pulse recovery means for increasing a potential of the low-frequency pulse gradually from a low level to a predetermined high level when the pulse applying body once having came off from the living body is pasted again on the living body.

4. A device according to claim 3, wherein the voltage pulse generating means comprises an inductor and means for periodically supplying a voltage to said inductor, and wherein the accumulating means comprises a capacitor.

5. A device according to claim 3, wherein the switching means comprises a first switching element which periodically applies the voltage pulses accumulated by the accumulating means to the first pulse applying body; and a second switching element which remains conductive and keeps the second pulse applying body grounded while the first switching element applies the voltage pulses.

6. A device according to claim 5, wherein the detecting current path comprises a series circuit including a resistance for converting the detecting current into a voltage, the first pulse applying body, the living body, the second pulse applying body and the second switching element in this order.

7. A device according to claim 6, wherein the pulse stopping means comprises a control means for stopping the operation of the voltage pulse generating means and for keeping the switching means off.

8. A device according to claim 7, wherein the pulse recovery means comprises judging means for judging that both of the pulse applying bodies are pasted back on the living body after at least one of the bodies comes off once; and time length changing means for, when the judging means judges both of the pulse applying bodies are pasted back, turning on and off alternately the voltage pulse generating means for a time length and for gradually extending the time length until the time length reaches a predetermined level.

9. A wireless low-frequency medical treatment device having a sending section for sending various data for low-frequency medical treatment and a pulse applying section for receiving the above data, for generating a low-frequency pulse corresponding to the data and for applying the pulse on a living body, the device being characterized in that the pulse applying section comprises:

a plurality of pulse applying bodies to be pasted on the living body, wherein said plurality of pulse applying bodies comprises a first applying body and a second applying body;

detecting means for detecting if at least one of the pulse applying bodies comes off from the living body wherein said detecting means comprises means for supplying a detecting current to said first and second applying bodies, wherein said detecting means detects whether at least one of the pulse applying bodies has come off from the living body based on whether said detecting current flows through a detecting current path including the living body and the first and second pulse applying bodies;

low-frequency pulse generating means for generating a low-frequency pulse to be supplied to the pulse applying bodies in accordance with data send from the sending section, wherein said low-frequency pulse generating means comprises voltage pulse generating means for generating voltage pulses periodically for a length of time determined by the data sent from the sending section, accumulating means for accumulating the voltage pulses, first and second switching means for alternately turning on and off a pulse supplying path which extends from the accumulating means to the first pulse applying body in order to supply the accumulated voltage pulses, and control means for selectively turning active one of said first and second switching means;

pulse stopping means for stopping generation of the low-frequency pulse when the detecting means detects that at least one of the pulse applying bodies comes off from the living body; and pulse recovery means for increasing a potential of the low-frequency pulse gradually from a low level to a predetermined high level when the pulse applying body once having come off from the living body is pasted again on the living body.

10. A device according to claim 9, wherein the voltage pulse generating means comprises an inductor and means for periodically supplying a voltage to said inductor, and wherein the accumulating means comprises a capacitor.

11. A device according to claim 9, wherein:

said first and second switching means each comprises a first switching element which is turned on and off alternately when one of said first and second switching means is turned active by the control means and a second switching element which is kept conductive while one of said first and second switching means is active;

the first switching element of the first switching means supplies the voltage pulses accumulated by the accumulating means to the first pulses accumulated by the accumulating means to the first pulse applying body when being turned on, and the first switching element of the second switching means supplies the voltage pulses accumulated by the accumulating means to the second pulse applying body when being turned on; and the second switching element of the first switching means grounds the second pulse applying body when being conductive, and the second switching element of the second switching means grounds the first pulse applying body when being conductive.

12. A device according to claim 11, wherein the detecting current path comprises a series circuit which includes a first resistance for converting a detecting current into a voltage, the first pulse applying body, the living body, the second pulse applying body, and the second switching element of the first switching means in this order when the first switching means is active; and comprises a series circuit which includes a second resistance for converting a detecting current into a voltage, the second pulse applying body, the living body, the first pulse applying body, and the second switching element of the second switching means in this order when the second switching means is active.

13. A device according to claim 12, wherein the pulse stopping means comprises a control circuit means for stopping the operation of the voltage pulse generating means and for keeping the first and the second switching means off.

14. A device according to claim 13, wherein the pulse recovery means comprises judging means for judging that both of the pulse applying bodies are pasted back on the living body after at least one of the bodies comes off once; and time length changing means for, when the judging means judges both of the pulse applying bodies are pasted back, turning on and off alternately the voltage pulse generating means for a time length and for gradually extending the time length until the time length reaches a predetermined level.

15. A device according to claim 2, wherein the low-frequency pulse generating means comprises voltage pulse generating means for generating voltage pulses periodically for a length of time determined by the data sent from the sending section; accumulating means for accumulating the voltage pulses; and switching means for alternately turning on and off a pulse supplying path which extends from the accumulating means to the first pulse applying body in order to supply the accumulated voltage pulses.

16. A device according to claim 15, wherein the voltage pulse generating means comprises an inductor and means for periodically supplying a voltage to said inductor, and wherein the accumulating means comprises a capacitor.

17. A device according to claim 15, wherein the switching means comprises a first switching element which periodically applies the voltage pulses accumulated by the accumulating means to the first pulse applying body; and a second switching element which remains conductive and keeps the second pulse applying body grounded while the first switching element applies the voltage pulses.

18. A device according to claim 17, wherein the detecting current path comprises a series circuit including a resistance for converting the detecting current into a voltage, the first pulse applying body, the living body, the second pulse applying body and the second switching element in this order.

19. A device according to claim 18, wherein the pulse stopping means comprises a control circuit means for stopping the operation of the voltage pulse generating means and for keeping the switching means off.

20. A device according to claim 19, wherein the pulse recovery means comprises judging means for judging that both of the pulse applying bodies are pasted back on the living body after at least one of the bodies comes off once; and time length changing means for, when the judging means judges both of the pulse applying bodies are pasted back, turning on and off alternately the voltage pulse generating means for a time length and for gradually extending the time length until the time length reaches a predetermined level.

21. A device according to claim 1, wherein:

said plurality of pulse applying bodies comprises a first applying body and a second applying body;

said detecting means comprises means for supplying a detector current to said first and second applying bodies, wherein said detecting means detects whether at least one of the pulse applying bodies has come off from the living body based on whether said detecting current flows through a detecting current path including the living body and the first and second pulse applying bodies; and said low-frequency pulse generating means comprises voltage pulse generating means for generating voltage pulses periodically for a length of time determined by the data sent form the sending section, accumulating means for accumulating the voltage pulses, first and second switch means for alternately turning on and off a pulse supplying path which extends from the accumulating means to the first pulse applying body in order to supply the accumulated voltage pulses, and control means for selectively turning active one of said first and second switching means.

22. A device according to claim 21, wherein the voltage pulse generating means comprises an inductor and means for periodically supplying a voltage to said inductor, and wherein the accumulating means comprises a capacitor.

23. A device according to claim 21, wherein:

said first and second switching means each comprises a first switching element which is turned on and off alternately when one of said first and second switching means is turned active by the control means and a second switching element which is kept conductive while one of said first and second switching means is active;

the first switching element of the first switching means supplies the voltage pulses accumulated by the accumulating means to the first pulse applying body when being turned on, and the first switching element of the second switching means supplies the voltage pulses accumulated by the accumulating means to the second pulse applying body when being turned on; and the second switching element of the first switching means grounds the second pulse applying body when being conductive, and the second switching element of the second switching means grounds the first pulse applying body when being conductive.

24. A device according to claim 23, wherein the detecting current path comprises a series circuit which includes a first resistance for converting a detecting current into a voltage, the first pulse applying body, the living body, the second pulse applying body, and the second switching element of the first switching means in this order when the first switching means is active; and comprises a series circuit which includes a second resistance for converting a detecting current into a voltage, the second pulse applying body, the living body, the first pulse applying body, and the second switching element of the second switching means in this order when the second switching means is active.

25. A device according to claim 24, wherein the pulse stopping means comprises a control circuit for stopping the operation of the voltage pulse generating means and for keeping the first and the second switching means off.

26. A device according to claim 25, wherein the pulse recovery mans comprises judging means for judging that both of the pulse applying bodies are pasted back on the living body after at least one of the bodies comes off once; and time length changing means for, when the judging means judges both of the pulse applying bodies are pasted back, turning on and off alternately the voltage pulse generating means for a time length and for gradually extending the time length until the time length reaches a predetermined level.

* * * * *